(12) United States Patent
Déverin

(10) Patent No.: US 6,483,642 B1
(45) Date of Patent: Nov. 19, 2002

(54) LIGHTING DEVICE FOR A SURGICAL MICROSCOPE

(75) Inventor: Jacques Alain Déverin, Widnau (CH)

(73) Assignee: Leica Microsystems AG, Heerbrugg (CH)

( * ) Notice: Subject to any disclaimer, the term of this patent is extended or adjusted under 35 U.S.C. 154(b) by 0 days.

(21) Appl. No.: 09/700,263

(22) PCT Filed: Mar. 25, 1999

(86) PCT No.: PCT/EP99/02151

§ 371 (c)(1),
(2), (4) Date: Nov. 9, 2000

(87) PCT Pub. No.: WO99/59016

PCT Pub. Date: Nov. 18, 1999

(30) Foreign Application Priority Data

May 13, 1998 (CH) ................................................ 1078/98

(51) Int. Cl.[7] ........................... G02B 21/06; G02B 21/00
(52) U.S. Cl. ........................ 359/389; 359/368; 359/385; 359/388
(58) Field of Search ................................ 359/368–390, 359/831–832, 431

(56) References Cited

U.S. PATENT DOCUMENTS

| | | | | |
|---|---|---|---|---|
| 4,789,228 A | * | 12/1988 | Le Pesant et al. | 359/831 |
| 5,627,613 A | * | 5/1997 | Kaneko | 351/221 |
| 5,760,952 A | * | 6/1998 | Koetke | 359/389 |
| 5,856,883 A | * | 1/1999 | Sander | 359/389 |
| 6,377,397 B1 | * | 4/2002 | Pensel et al. | 359/389 |

FOREIGN PATENT DOCUMENTS

| | | | | |
|---|---|---|---|---|
| DE | 93 14 578 U | | 1/1994 | |
| DE | 196 50 773 A | | 7/1997 | |
| FR | 2 666 662 A | | 3/1992 | |
| JP | 56-146113 | * | 11/1981 | 359/385 |
| JP | 09 105866 A | | 4/1997 | |
| JP | 10-133122 | * | 5/1998 | 359/385 |

* cited by examiner

Primary Examiner—Thong Nguyen
(74) Attorney, Agent, or Firm—Hodgson Russ LLP

(57) ABSTRACT

The invention relates to an illumination device for a surgical microscope comprising a main objective lens (1) surrounding a main optical axis (6) and an illumination optical system (2) having a light source (3). Two prisms (4, 5) are provided between the main objective lens (1) and the illumination optical system (2). During operation, the first prism (4) causes part of the light flow from the illumination optical system (2) to be deflected at a small angle to the main optical axis (6) and the second prism (5) causes another part of the light flow from the illumination optical system (2) to be deflected along the main optical axis (6). Both prisms (4, 5) are arranged next to each other. The light entry surfaces (7) of both prisms face the illumination optical system (2) in such a way that light flux can be independently adjusted for the two prisms (4, 5). This results in a compact design and a good light flux distribution.

14 Claims, 1 Drawing Sheet

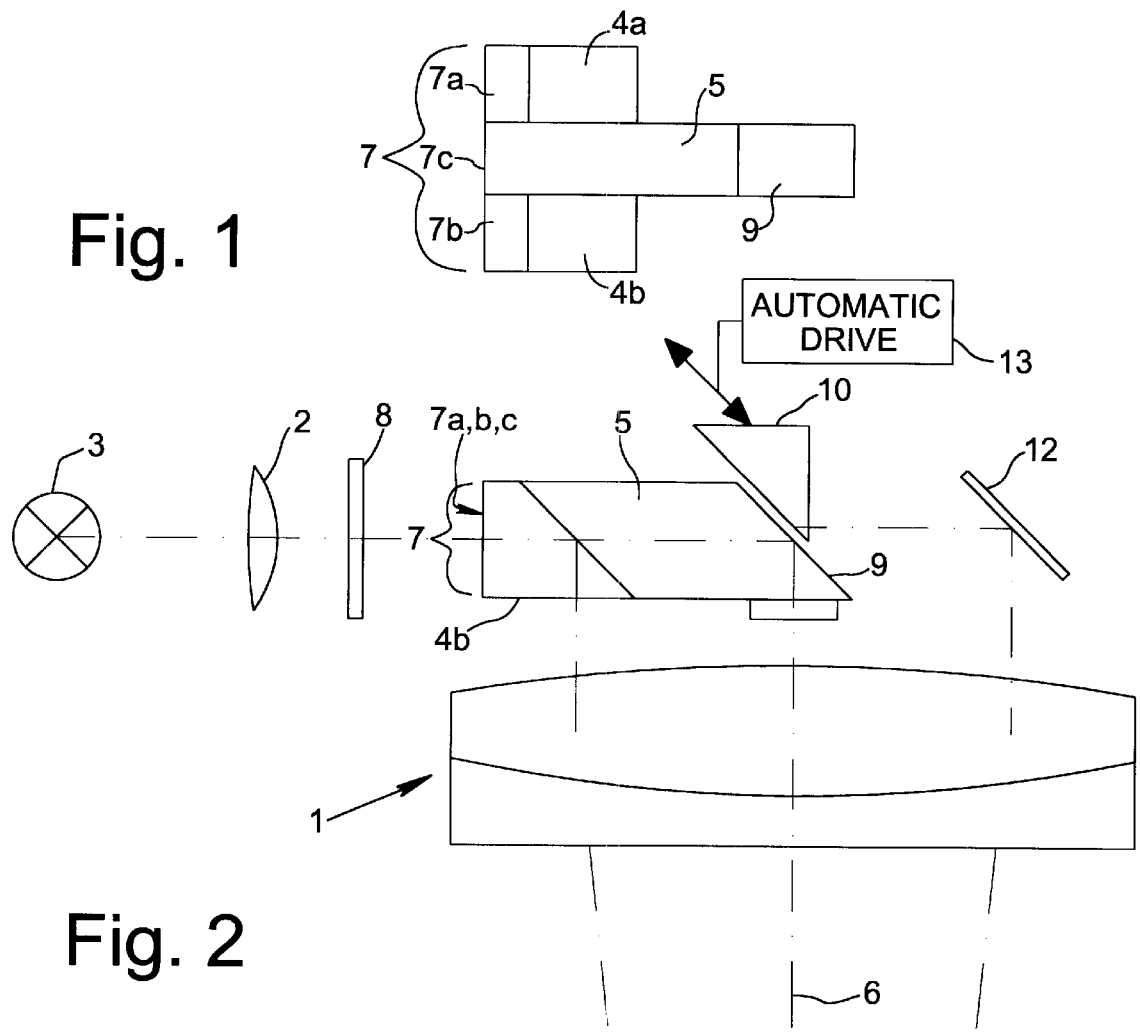
Fig. 1
Fig. 2
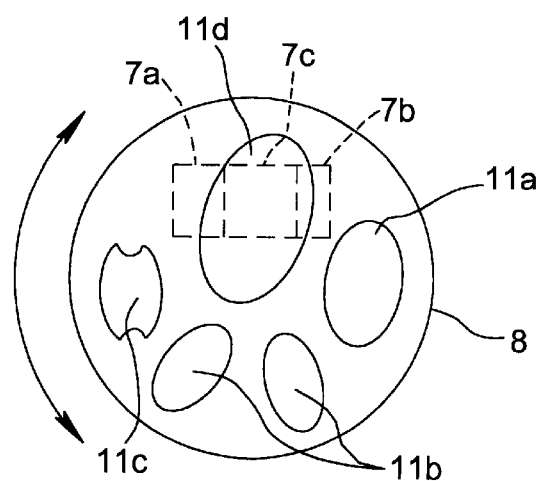
Fig. 3
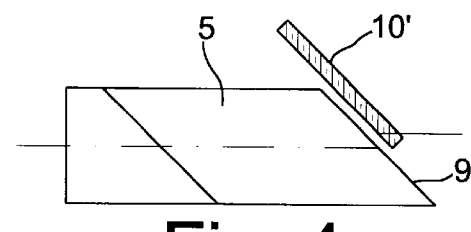
Fig. 4
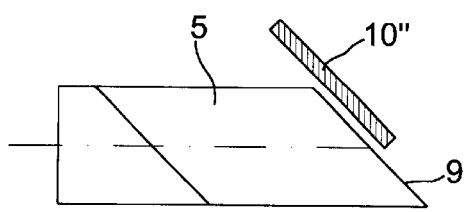
Fig. 5

LIGHTING DEVICE FOR A SURGICAL MICROSCOPE

CROSS-REFERENCES TO RELATED APPLICATIONS

The present application is the U.S. national phase under 35 U.S.C. 371 of International Application No. PCT/EP99/02151 filed Mar. 25, 1999 claiming priority of Swiss Patent Application No. 1078/98 filed May 13, 1998.

BACKGROUND OF THE INVENTION

1. Field of the Invention

The invention concerns an illumination system for a surgical microscope. Quite varied illumination systems are known in microscopy. Illumination is a particularly difficult subject in surgical microscopy, and, there, especially, in ophthalmology. That is because optimal illumination can be critical for surgical success and also because the light intensity under the microscope cannot be made as high as might be desired because of danger to the tissue.

2. Description of the Related Art

German Patent C2-40 28 605 and its family member, U.S. Pat. No. 5,126,877, present a known illumination system. A still older illumination system which works well, was marketed in 1985 by the applicant's predecessor company as "0° Illumination System" (see the Wild Heerbrugg AG brochure M1 668d-X.85 of Oct. 1985).

In this design, the entire light beam is deflected from an illumination optical system with its lamp by a first prism, from a perpendicular to the optical axis of the main objective of the microscope into an oblique beam at a small angle (e. g., 6°) from the optical axis. This is the main illumination of the surgical field. But, to get the "0° illumination" particularly desired for eye surgery because of the "red reflection" which it produces, a transparent disk parallel to the principal plane of the main objective is placed between the first prism and the main objective. This disk can be rotated about the main axis. The disk carries a second prism, which is relatively narrow in comparison with the first one. This second prism moves part of the light beam diverted by the first prism into the main axis by means of two approximately parallel mirror surfaces.

Thus, rotation of the mirror can optionally add "0° illumination" to standard illumination at a small angle to the main axis. That process reduces the light flux of the standard illumination in proportion to the light flux which it uses. Theoretically, it is possible to control the distribution of the light by the angular position about the main axis.

As well proven as this known design is, there has been a great desire for newer solutions which work without rotating disks. The solution of the German C and U.S. patents cited was noted initially as one such solution.

A significantly more recent design is reported in Japanese Patent Application 9-105866. It is somewhat comparable with the old "0° Illumination" of the predecessor of the applicant, in that it has, below the first prism, a second prism with two mirror surfaces, but it does not rotate about the main axis. This design gives a fundamentally constant division of the light flux between the 0° portion and the larger portion that is permanently incident at a small angle. Apparently it is possible to reduce the joint light flux by a diaphragm which can be inserted into the beam path of the illumination optical system.

This Japanese design has in common with the "0° Illumination" that two prisms are placed in succession, so that both require a certain distance in front of the main objective. In addition, control of the light flux in the main axis region necessarily changes the light flux which is incident on the object at a small angle.

One of those effects, and preferably the other also, are intended to be avoided according to the invention.

The object of the invention, then, is to provide a compact illumination system with at least one oblique (with respect to the main axis) light flux and at least one parallel light flux, so that as much as possible the two light fluxes can be controlled independently of each other.

SUMMARY OF THE INVENTION

This object is attained, for the first time, by an illumination system according to the present invention. The illumination system generally comprises an illumination means for providing an illumination beam of light along an illumination optical axis, and a plurality of prisms located to receive and divert respective portions of the illumination beam through the objective lens of the microscope either along the main optical axis of the objective lens or at a small angle relative thereto.

An elegant solution with symmetric illumination of the object includes a central prism for diverting a portion of the illumination beam along the main optical axis, and a pair of prisms located on each opposite side of the central prism for diverting portions of the illumination beam at a small angle to the main optical axis, wherein the three prisms have a combined light entry surface area facing the illumination beam that essentially admits the entire illumination beam when unblocked.

The present invention gives a small height, as the prisms are now side by side. It also assures that the light entry areas of the two prisms can be supplied with a partial flux of light independently of each other, so that each of these partial light fluxes can be controlled independently of the other.

Placing an adjustable diaphragm between the illumination optical system and at least one light entry surface of at least one prism presents an example of one such potential for regulation. Adjustable diaphragms such as an opaque disk with windows which can be selectively placed so as to allow the illumination beam to enter different light entry surfaces to different extents, as needed, are simply adjustable diaphragms. An LCD which, under electronic control, allows freely selectable portions to enter the light entry surfaces is a particularly user-friendly diaphragm. LCDs can be used as gray filters by selective darkening. On the other hand, electronically stored window shapes can be used to provide quite varied illumination adjustments.

The invention is not limited to these stated diaphragms, though. It can instead be equipped with any known or novel system for light control without losing its essential feature, the flat, compact design and the ability to control independently.

In a particular embodiment and possibly an alternative to those described previously, at least one light-interrupting part is positioned at at least one of the reflective surfaces of the prisms, in such a way that the light-interrupting part can be moved or swiveled with electronic means, or can be electro-optically controlled so as to refract the total reflection. It can reasonably be used alternatively or even in combination. If needed, it also leads to an improved and even more symmetric illumination.

The term "light-interrupting part" is understood to mean any element in which total reflection is eliminated at the contact site when in contact with a total reflection surface. They could, for example, be prisms, glass plates, or even certain, possibly non-transparent, plastic or metal plates or liquids. This particular embodiment provides not only the possibility for light control, but also the possibility for dividing a light flux for use of another optional mirror element to produce another illumination beam at an angle to the main axis. There is another preferred embodiment in which only the "0° Illumination" is controlled by using the interruption of total reflection or, in case the light flux is diverted out of the second prism, it is directed to another oblique illumination beam independent of the first oblique illumination beam.

According to the invention, a means for controlling the color of the light can also be provided, independently of, or in addition to, the light flux regulation.

BRIEF DESCRIPTION OF THE DRAWINGS

The invention is explained in more detail with the drawing. The drawing shows:

FIG. 1: a plan view of the essential elements of the invention;

FIG. 2: an expanded side view with a schematic illumination optical system and the main objective;

FIG. 3: an example of an aperture disk according to the inventions

FIG. 4: a partial side view showing a variation of the present invention, wherein a light-interrupting part thereof is a glass plate shown in cross-section in the view; and FIG. 5: a partial side view showing a variation of the present invention, wherein a light-interrupting part thereof is an opaque component shown in cross-section in the view.

DETAILED DESCRIPTION OF THE PREFERRED EMBODIMENTS

The figures are described together. Identical reference symbols indicate identical parts. Identical reference symbols with different indices indicate parts with identical or similar functions.

A two-part first prism 4a and 4b is at the sides of a second prism 5. They can, for example, be cemented together. Each prism has one light entry surface 7, which faces an illumination optical system 2. A light source 3 is shown as an example. It could quite well also be a light guide. The division of prism 4 into two parts is not essential, but preferred, because that gives good symmetry of the illumination. The arrangement can also be asymmetrical.

An adjustable diaphragm 8 can optionally be placed between the illumination optical system 2 and the light entry surface 7. The diaphragm can, for instance, appear as shown in FIG. 3. There one can see windows 11a–11d, which can be placed, as desired, in front of the light entry surface 7. In FIG. 3, window 11d is placed in front of the light entry surface 7c of the second prism, so that in this case only 0° illumination is active at fall intensity. Both of the first prism parts 4a and 4b get practically no light flux. If one were to turn the window 11d somewhat farther, that could produce a division of the light flux between the light entry surface 7c and one of the two light entry surfaces, 7a or 7b.

Windows 11b are provided as an obvious alternative. They allow complete cutoff of the 0° illumination with simultaneous full illumination of the first prism 4. Windows 1 1a allow full illumination of all the prisms 4, 5; and window 11c allows full illumination of prism 5 with simultaneous reduction of the illumination to the first prism 4.

Prism 4a,b, could also be designed throughout as a single piece, so that prism 4 covers the entire entry surface 7a,b,c. Then prism 5 would be a narrower prism cemented to the hypotenuse of prism 4. Obviously, prisms 4 and 5 could also be made as a single one-piece prism.

Independently of diaphragm 8, a slidable prism 10 is also provided as a light interruption part. Its plane surface can be slid along the total reflection surface 9 of the second prism 5, with automatic drive means 13 preferably being provided for moving or rotating prism 10. Although this is not shown in detail, it can, for instance, be pressed against surface 9 by a spring. Because of the interruption of the total reflection, part of the light flux from the second prism 5 is not reflected through the main objective 1, but is taken out from the second prism 5 by the light interruption part 10. As shown in FIG. 4, the light-interrupting part can also be embodied as a glass plate 10'. In another variation illustrated at FIG. 5, the light-interrupting part is embodied as an opaque component 10", such as a plastic or metal plate.

In this case, a liquid film, especially an oil film, on the contact surface could be helpful. In a variation, not shown, that could result in destruction of the light, for instance, if the right surface of the light interruption part 10 is colored black, or if this surface is transparent, but directed toward a black interior coating of the microscope tube.

The total reflection can also be interrupted, within the meaning of the invention, by electro-optical layers (e. g., LCD, crystal, or vapor-deposited coatings) between the two prisms. These layers could, to the extent that they can be selectively activated electronically, make the desired areas totally reflecting or nonreflecting.

In the present example embodiment, though, this surface is directed toward another mirror surface 12, which redeflects the deflected light flux through the main objective 1 onto the object at a small angle relative to the main optical axis 6 of the objective 1. If necessary, the other mirror surface could also be adjustable so as to affect the angle of reflection, but that is not shown in detail.

What is claimed is:

1. An illumination system for a surgical microscope for illuminating an object to be viewed, said microscope having a main objective lens aligned on a main optical axis, said illumination system comprising:

illumination means including a light source for providing an illumination beam of light along an illumination optical axis; and three prisms placed between said main objective and said light source, each of said three prisms including a light admission surface, said three prisms being arranged side-by-side such that said light admission surfaces are in a single plane intersected by said illumination optical axis, two of said three prisms operating to divert part of said illumination beam at a small angle to said main optical axis of said objective lens and a remaining one of said three prisms operating to divert another part of said illumination beam along said main optical axis;

wherein said three prisms have a combined light admission surface area facing said illumination beam.

2. The illumination system according to claim 1, wherein said two of said three prisms are placed at opposite sides of said remaining one of said three prisms to produce symmetric illumination of said object.

3. The illumination system according to claim 1, further comprising an aperture diaphragm placed between said illumination means and at least one light admission surface of at least one of said three prisms.

4. The illumination system according to claim 3, wherein said aperture diaphragm is an opaque disk including a plurality of light-transmitting windows that can be selectively placed in said illumination optical axis to control light flux entering respective light admission surfaces of said three prisms.

5. The illumination system according to claim 3, wherein said aperture diaphragm is an LCD electronically controlled to allow selectable portions of said illumination beam to enter respective light admission surfaces of said three prisms.

6. The illumination system according to claim 1, wherein each of said three prisms includes a reflective surface for diverting an incident part of said illumination beam, and said illumination system further comprises a light-interrupting element associated with at least one of said reflective surfaces for interrupting total reflection at said associated reflective surface.

7. The illumination system according to claim 6, further comprising automatic means for moving said interrupting element.

8. The illumination system according to claim 6, wherein said light-interrupting element is electro-optically controlled.

9. The illumination system according to claim 6, wherein said light-interrupting element is a transparent prism.

10. The illumination system according to claim 6, wherein said light-interrupting element is a glass plate.

11. The illumination system according to claim 6, wherein said light-interrupting element is an opaque component.

12. The illumination system according to claim 6, further comprising another reflective surface for diverting rays emerging from said light-interrupting element at an angle relative to said main optical axis.

13. The illumination system according to claim 6, wherein said light-interrupting element is associated with said reflective surface of said remaining one of said three prisms.

14. The illumination system according to claim 1, further comprising a color-selecting filter means placed between said illumination means and at least one light admission surface of at least one of said three prisms for controlling the color of said illumination beam.

* * * * *